United States Patent
Chen et al.

(10) Patent No.: US 12,319,686 B2
(45) Date of Patent: Jun. 3, 2025

(54) PROCESS FOR THE PREPARATION OF TETRAHYDROPYRIDOPYRIMIDINES

(71) Applicant: Hoffmann-La Roche Inc., Little Falls, NJ (US)

(72) Inventors: Junli Chen, Shanghai (CN); Weichun Chen, Shanghai (CN); Lin Wang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 767 days.

(21) Appl. No.: 17/423,069

(22) PCT Filed: Jan. 16, 2020

(86) PCT No.: PCT/EP2020/050951
§ 371 (c)(1),
(2) Date: Jul. 14, 2021

(87) PCT Pub. No.: WO2020/148352
PCT Pub. Date: Jul. 23, 2020

(65) Prior Publication Data
US 2022/0098189 A1    Mar. 31, 2022

(30) Foreign Application Priority Data
Jan. 17, 2019   (WO) ................ PCT/CN2019/072102

(51) Int. Cl.
*C07D 471/04*   (2006.01)

(52) U.S. Cl.
CPC ................ *C07D 471/04* (2013.01)

(58) Field of Classification Search
CPC .................................................. C07D 471/04
See application file for complete search history.

(56) References Cited

U.S. PATENT DOCUMENTS

| | | | |
|---|---|---|---|
| 7,977,342 B2 | 7/2011 | Simmen et al. | |
| 9,434,725 B2 | 9/2016 | Do et al. | |
| 9,487,533 B2 | 11/2016 | Castanedo et al. | |
| 9,845,322 B2 | 12/2017 | Cheng et al. | |

FOREIGN PATENT DOCUMENTS

| | | | |
|---|---|---|---|
| JP | 2008-514678 A | 5/2008 | |
| JP | 2010-512337 A | 4/2010 | |
| JP | 2015-521645 A | 7/2015 | |
| WO | 02/064574 A2 | 8/2002 | |
| WO | 2006/035061 A1 | 4/2006 | |
| WO | 2008/013414 A1 | 1/2008 | |
| WO | 2010/097092 A1 | 9/2010 | |
| WO | 2010/135650 A1 | 11/2010 | |
| WO | 2012/052948 A1 | 4/2012 | |
| WO | 2013/001445 A1 | 1/2013 | |
| WO | 2013/049352 A2 | 4/2013 | |
| WO | 2014/097148 A1 | 6/2014 | |
| WO | 2016/107832 A1 | 7/2016 | |
| WO | WO 2016/177655 A1 * | 11/2016 | |
| WO | 2017/025727 A1 | 2/2017 | |
| WO | WO 2018/001952 A1 * | 1/2018 | |
| WO | 2020/148352 A1 | 7/2020 | |

OTHER PUBLICATIONS

Asahina, Y et al., "Synthesis and Antibacterial Activity of the 4-Quinolone-3-carboxylic Acid Derivatives Having a Trifluoromethyl Group as a Novel N-1 Substituent" ACS J Med Chem 48(9):3443-3446 (Apr. 13, 2005).
Geng et al., "Small-molecule inhibitors for the treatment of hepatitis B virus documented in patents" Mini Reviews in Medicinal Chemistry 13(5):749-776 ( 2013).
International Preliminary Report on Patentability (IPRP) for PCT/EP2017/065690 issued on Jan. 1, 2019.
International Preliminary Report on Patentability—PCT/EP2020/050951, pp. 1-6 (Jun. 16, 2021).
International Search Report for PCT/EP2017/065690 mailed on Jul. 31, 2017.
International Search Report—PCT/EP2020/050951, (w/Written Opinion),:pp. 1-10 (Apr. 30, 2020).
I.V, X., et al., "CuI catalyzed C—N bond forming reactions between aryl/heteroaryl bromides and imidazoles in [Bmim]BF4" Tetrahedron 62(20):4756-4761 (May 15, 2006).

* cited by examiner

*Primary Examiner* — Brenda L Coleman
(74) *Attorney, Agent, or Firm* — Genentech, Inc.

(57) ABSTRACT

The present invention relates to a process for synthesizing a compound of formula (I), or a pharmaceutically acceptable salt thereof, which is useful for prophylaxis and treatment of a viral disease in a patient relating to hepatitis B infection or a disease caused by hepatitis B infection.

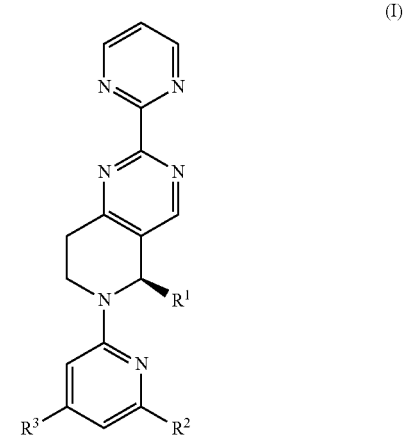

(I)

28 Claims, No Drawings

PROCESS FOR THE PREPARATION OF TETRAHYDROPYRIDOPYRIMIDINES

CROSS-REFERENCE TO RELATED APPLICATIONS

This application is a continuation of International Application No. PCT/EP2020/050951 filed Jan. 16, 2020, which claims prior it to International Application, PCT/CN2019/072102 filed Jan. 17, 2019 both of which are incorporated by reference in their entirety.

The present invention relates to a process for the preparation of compounds of formula (I),

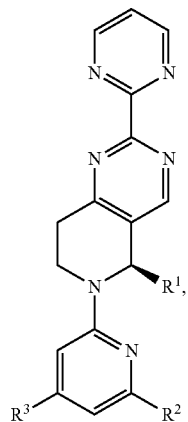

(I)

wherein $R^1$ is $C_{1-6}$alkyl; $R^2$ is $C_{1-6}$alkyl or halogen; $R^3$ is $C_{1-6}$alkyl or $C_{1-6}$alkoxy.

Particularly, the present invention relates to a process for the preparation of (5R)-6-(6-fluoro-4-methoxy-2-pyridyl)-5-methyl-2-pyrimidin-2-yl-7,8-dihydro-5H-pyrido[4,3-d]pyrimidine,

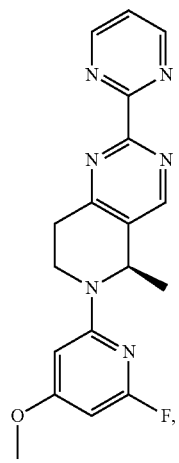 [SMILES: COc1cc(F)nc(N2CCc3nc(-c4ncccn4)ncc3[C@H]2C)c1]

or a pharmaceutically acceptable salt.

BACKGROUND OF THE INVENTION

The previous synthetic approach of compounds of formula (I) was disclosed in patent WO2016/177655, however, it is not suitable for commercial manufacturing due to the following issues:

(a) The overall yield for making the compound (I) is very low (only ~1.5%) and has scalability concerns as indicated in the patent due to several steps with low reaction yield and regioselective synthesis concerns.

(b) The column purifications are needed for the critical intermediates, which are 8-(6-fluoro-4-methoxy-2-pyridyl)-1,4-dioxa-8-azaspiro[4.5]decane, 1-(6-fluoro-4-methoxy-2-pyridyl)piperidin-4-one and 6-(6-fluoro-4-methoxy-2-pyridyl)-2-pyrimidin-2-yl-7,8-dihydro-5H-pyrido[4,3-d]pyrimidine.

(c) All intermediates are regio-isomers, therefore extensive HPLC purification for these intermediates are required to make the sale-up synthesis becoming very challenge.

(d) Scalability and cost concern for the production because of the oxidation reaction used expensive $RuCl_3/NaIO_4$ in a huge volume of solvent, which leads to low efficiency overall.

Based on the issues above, one object of this invention therefore is to find an alternative efficient synthetic approach which can be applied on a technical scale and/or result in obtaining the product in a higher yield and/or desired purity. Addressing all these issues (a) to (d) mentioned above is also one of the objects for this invention.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, butyl, isobutyl, tert-butyl and the like. Particular "$C_{1-6}$alkyl" group is methyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "$C_{1-6}$alkoxy" group is methoxy.

The term "halogen" and "halo" are used interchangeably herein and denote fluoro, chloro, bromo, or iodo.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include, for example, those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., *Organic Process*

Research & Development 2000, 4, 427-435. Particular are the sodium salts of the compounds of formula (I).

Abbreviations

ACN Acetonitrile
eq Equivalent
DCM Dichloromethane
DIPEA N,N-Diisopropylethylamine
MeOH Methanol
EtOH Ethanol
IPA Isopropanol
IPAc Isopropyl acetate
MTBE Methyl tert-butyl ether
Et$_2$O Diethyl ether
TEA Triethylamine
AcOH Acetic acid
DBU 1,8-Diazabicyclo[5.4.0]undec-7-ene
NMM N-methylmorpholine
t-BuONa Sodium tert-butoxide
LDA Lithium diisopropylamide
LiHMDS Lithium bis(trimethylsilyl)amide
NaHMDS Sodium bis(trimethylsilyl)amide
NaBH$_4$ Sodium borohydride
TFA Trifluoroacetic acid
THF Tetrahydrofuran
MeTHF 2-Methyl Tetrahydrofuran
DMF N,N-Dimethylformamide
DMAc N,N-Dimethylacetamide
DMSO Dimethyl sulfoxide
NMP 1-Methyl-2-pyrrolidinone
V volume
wt % weight percent The present invention provides a process for preparing the compounds of formula (I) as outlined in the scheme 1.

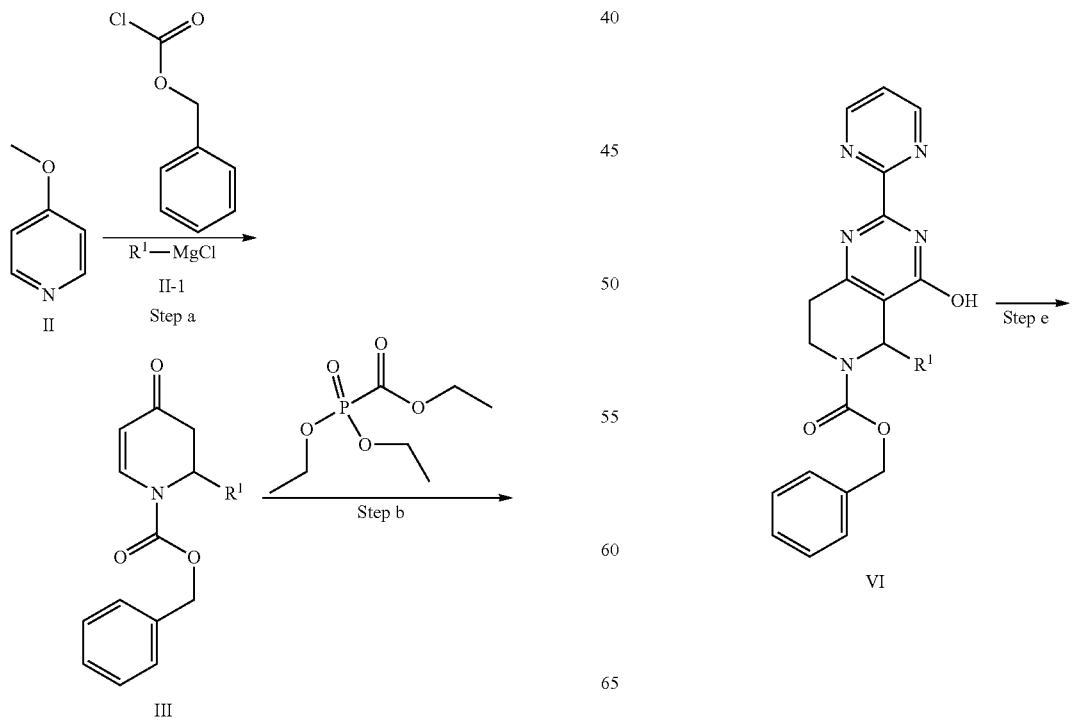

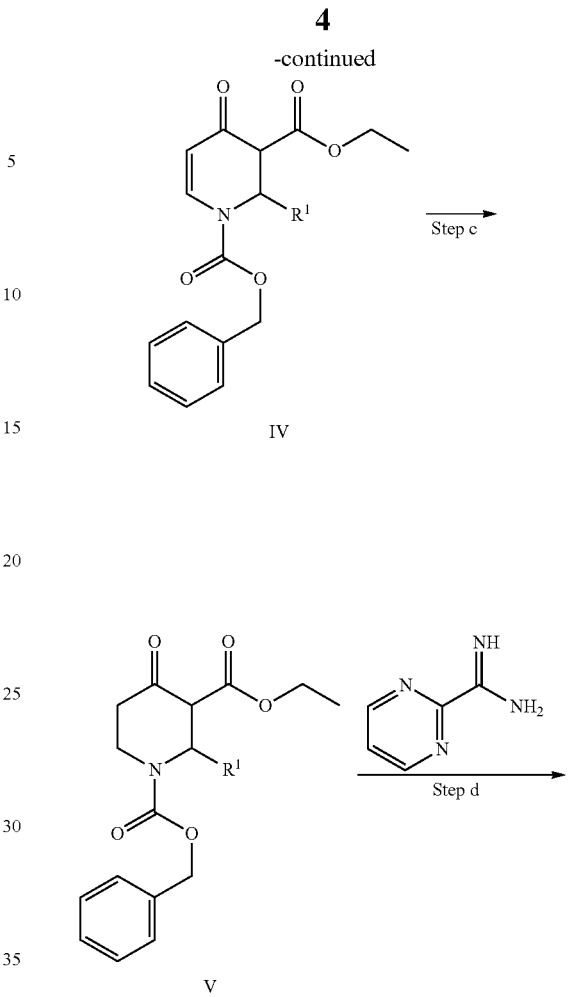

The synthesis comprises one or more of the following steps:

step a) the formation of the dihydropyridine (III),

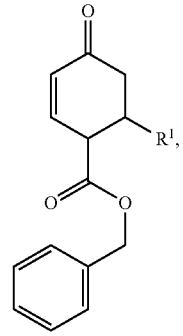

(III)

wherein $R^1$ is $C_{1-6}$alkyl;

step b) the formation of the compound of formula (IV) via the alkylation reaction of the dihydropyridine (III) and ethyl diethoxyphosphorylformate,

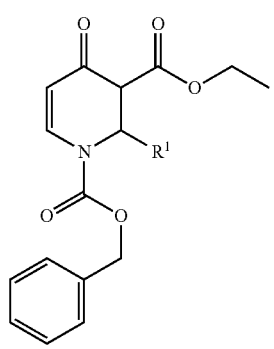

(IV)

wherein $R^1$ is $C_{1-6}$alkyl;

step c) the formation of the piperidine (V) via the reduction reaction of the compound of formula (IV),

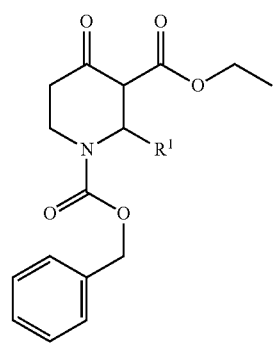

(V)

wherein $R^1$ is $C_{1-6}$alkyl;

step d) the formation of the compound of formula (VI) via the cyclization reaction of the piperidine (V) and pyrimidine-2-carboxamidine,

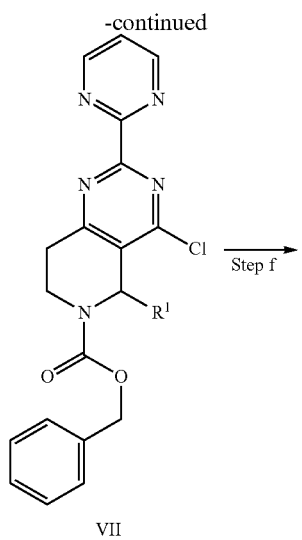

VII

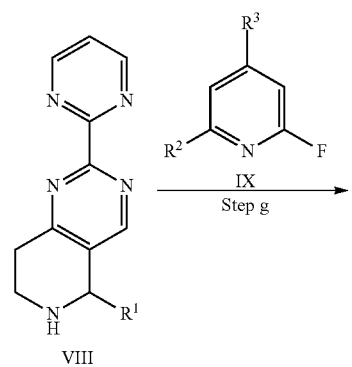

VIII

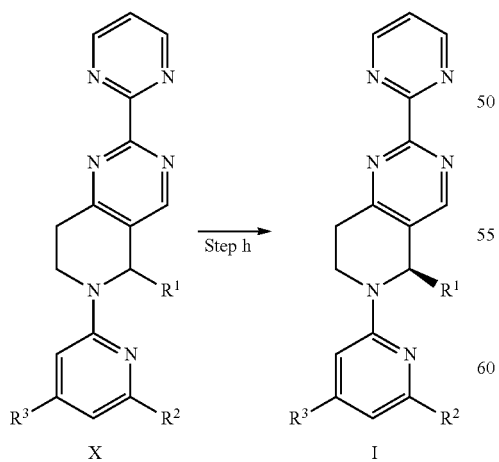

X

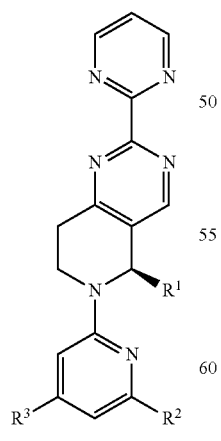

I wherein $R^1$ is $C_{1-6}$alkyl; $R^2$ is $C_{1-6}$alkyl or halogen; $R^3$ is $C_{1-6}$alkyl or $C_{1-6}$alkoxy.

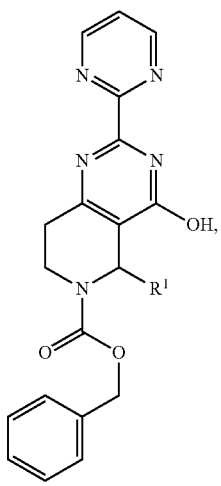

(VI)

wherein R¹ is $C_{1-6}$alkyl;

step e) the formation of the compound of formula (VII) via chloration of the compound of formula (VI),

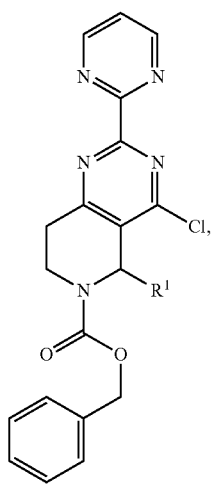

(VII)

wherein R¹ is $C_{1-6}$alkyl;

step f) the formation of the compound of formula (VIII) via selective hydrogenation of the compound of formula (VII),

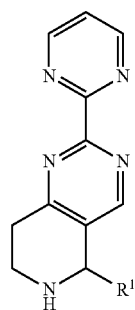

(VIII)

wherein R¹ is $C_{1-6}$alkyl;

step g) the formation of the compound of formula (X) by N-alkylation of the compound of formula (VIII) with the compound of formula (IX),

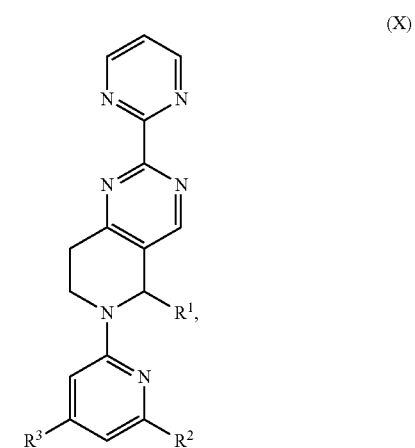

(X)

wherein R¹ is $C_{1-6}$alkyl; R² is $C_{1-6}$alkyl or halogen; R³ is $C_{1-6}$alkyl or $C_{1-6}$alkoxy;

step h) SFC separation of the compound of formula (X) to afford the compound of formula (I),

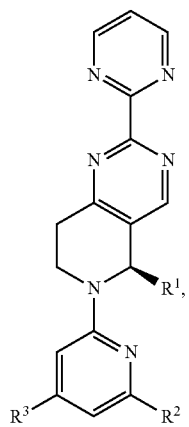

(I)

wherein R¹ is $C_{1-6}$alkyl; R² is $C_{1-6}$alkyl or halogen; R³ is $C_{1-6}$alkyl or $C_{1-6}$alkoxy.

In another embodiment of this invention, wherein R¹ is methyl; R² is F or methyl; and R³ is methyl or methoxy.

In another embodiment of this invention, wherein R¹ is methyl; R² is F; and R³ is methoxy.

A detailed description of the present invention of process steps is as following:

Step a) Alkylation reaction to form the dihydropyridine (III).

The formation of the dihydropyridine (III) is performed in the presence of a suitable metal reagent and a suitable organic solvent. The conversion as a rule is performed under a cooling condition.

The suitable metal reagent is selected from methyl, ethyl and isopropyl Grignard reagent. Particularly the metal reagent is methyl Grignard reagent.

The suitable organic solvent is selected from MTBE, THF, Et₂O and Me-THF. Particularly the organic solvent is THF.

The temperature of the alkylation reaction as a rule is performed at −30° C.-0° C. Particularly temperature of the reaction is performed at −10° C.-0° C.

Step b) C-alkylation reaction to form the compound of formula (IV).

The formation of compound of formula (IV) is performed in the presence of a suitable base and a suitable organic solvent. The conversion as a rule is performed under a cooling condition.

The suitable base is selected from t-BuONa, LDA, LiHMDS and NaHMDS. Particularly the base is LiHMDS.

The suitable organic solvent is selected from MTBE, THF, $Et_2O$ and MeTHF. Particularly the organic solvent is THF.

The temperature of the C-alkylation reaction as a rule is performed at 0° C.-25° C. Particularly temperature of the reaction is performed at 0° C.-5° C.

Step c) Reduction reaction to form the piperidine (V).

The formation of the piperidine (V) is performed in the presence of a suitable reductive reagent and a suitable organic solvent. The conversion as a rule is performed under a heating condition.

The suitable reductive reagent is selected from Fe powder, Zn powder and $NaBH_4$. Particularly the reagent is Zn powder.

The suitable organic solvent is selected from MeOH, EtOH, AcOH and formic acid. Particularly the organic solvent is AcOH.

The temperature of the reductive reaction as a rule is performed at 55° C.-80° C. Particularly temperature of the reductive reaction is performed at 65° C.-70° C.

Step d) Condensation reaction to form the compound of formula (VI).

The formation of compound of formula (VI) is performed in the presence of a suitable base and a suitable organic solvent. The conversion as a rule is performed under a heating condition.

The suitable base is selected from DIPEA, $Cs_2CO_3$, $K_2CO_3$ and $K_3PO_4$. Particularly the base is $K_2CO_3$.

The suitable organic solvent is selected from isopropyl alcohol, methanol, trifluoroethanol and ethanol. Particularly the organic solvent is trifluoroethanol.

The temperature of the condensation reaction as a rule is performed at 60° C.-80° C. Particularly temperature of the reaction is performed at 65° C.-70° C.

Step e) Chloration reaction to form the compound of formula (VII).

The formation of compound of formula (VII) is performed in the presence of a suitable base and a suitable organic solvent. The conversion as a rule is performed under a heating condition.

The suitable base is selected from TEA, DIPEA and tripropylamine. Particularly the base is tripropylamine.

The suitable organic solvent is selected from DCM, MTBE, toluene and 1,2-dimethoxyethane. Particularly the organic solvent is toluene.

The temperature of the chloration reaction as a rule is performed at 50° C.-80° C. Particularly temperature of the reaction is performed at 55° C.-60° C.

Step f) Hydrogenation reaction to form the compound of formula (VIII).

The formation of compound of formula (VIII) is performed in the presence of a suitable base and a suitable organic solvent. The conversion as a rule is performed under a heating condition.

The suitable base is selected from DIPEA, tripropylamine, $NH_3·H_2O$ and TEA. Particularly the base is $NH_3·H_2O$.

The suitable organic solvent is selected from IPAc, isopropyl alcohol, ethanol and methanol. Particularly the organic solvent is ethanol.

The temperature of the formylation reaction as a rule is performed at 20° C.-40° C., Particularly temperature of the reaction is performed at 25° C.-30° C.

Step g) N-alkylation reaction to form the compound of formula (X).

The formation of compound of formula (X) is performed in the presence of a suitable base in a suitable organic solvent. The conversion as a rule is performed under a heating condition.

The suitable base is selected from DIPEA, TEA, tripropylamine, 2,2,6,6-tetramethylpiperidine, N,N-dicyclohexylmethylamine, DBU, NMM, triethanolamine, pyridine, potassium tert-butylate, magnesium tert-butylate, $K_3PO_4$, $K_2CO_3$, $Cs_2CO_3$, CsF and CaO. Particularly the base is $K_3PO_4$ or CsF. Most particularly the base is CsF.

The suitable organic solvent is selected from IPA, trifluoroethanol, 4-Methyl-2-pentanol, 1,2-propandiol, ACN, DMF, DMAc, DMSO, sulfolane, NMP, pyridine and 1-butyl-3-methylimidazolium tetrafluoroborate. Particularly the organic solvent is NMP or 1-butyl-3-methylimidazolium tetrafluoroborate. Most particularly the organic solvent is 1-butyl-3-methylimidazolium tetrafluoroborate.

The temperature of the substitution reaction as a rule is performed at the temperature between 90° C. and 120° C. Particularly temperature of the reaction is performed at temperature between 90° C. and 100° C.

Step h) SFC separation of the compound of formula (X) to afford the compound of formula (I).

The compound of formula (I) is separated out in the presence of a chiral column and a suitable organic solvent. The conversion as a rule is performed under a heating condition.

The suitable chiral column is selected from Chiralcel OD and CHIRALPAK AD-3, Particularly the chiral column is Chiralcel OD, 300×50 mm I.D., 10 um.

The suitable solvent is selected from MeOH, EtOH, 95% EtOH and isopropyl alcohol. Particularly the solvent is methanol.

The temperature of the intermolecular reaction as a rule is performed at 30° C.-45° C. Particularly temperature of the reaction is performed at 35° C.-40° C.

EXAMPLES

The invention is illustrated further by the following examples. They should not, however, be construed as limiting the scope of the invention.

General Experimental Conditions

LC-MS high resolution spectra were recorded with an Agilent LC-system consisting of Agilent 1290 high pressure gradient system, a CTC PAL auto sampler and an Agilent 6520 QTOF. The separation was achieved on a Zorbax Eclipse Plus C18 1.7 μm 2.1×50 mm column at 55° C.; A=0.02% formic acid in Water; B=acetonitrile with 0.01% formic acid at a flow rate of 0.8 mL/min. gradient: 0 minute 5% B, 0.3 minute 5% B, 4.5 minutes 99% B, 5 minutes 99% B. The injection volume was 2 μL. Ionization was performed in Agilents Multimode source. The mass spectrometer was run in "2 GHz extended dynamic range" mode, resulting in a resolution of about 10 000 at m/z=922. Mass accuracy was ensured by internal drift correction. Mass spectra (MS): generally only ions which indicated the parent mass were reported, and unless otherwise stated the mass ion quoted was the positive mass ion (M+H)+.

NMR Spectra were obtained on a Bruker 400 MHz Avance III spectrometer equipped with a 5 mm TCI cryoprobe.

All reactions involving air-sensitive reagents were performed under a nitrogen atmosphere. Reagents were used as received from commercial suppliers without further purification unless otherwise noted.

Example 1

Benzyl 2-methyl-4-oxo-2,3-dihydropyridine-1-carboxylate

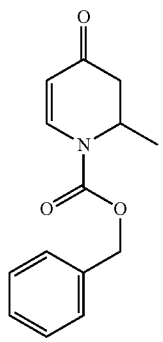 [SMILES: CC1CC(=O)C=CN1C(=O)OCc1ccccc1]

Preparation of Benzyl 2-methyl-4-oxo-2,3-dihydropyridine-1-carboxylate

To a 5 L jacket reactor was charged with 4-methoxypyridine (170 g, 1.56 mol) and THF (2.55 L) at room temperature under $N_2$ atmosphere. The mixture was cooled to −5~−10° C. using Huber chiller. To the stirred mixture was charged with benzyl carbonochloridate (279 g, 1.64 mol) at −5~−10° C. in 10~15 minutes, the white solid appeared once addition. The mixture was agitated using a magnetic stirrer at −5~−10° C. for another 10 minutes. To the mixture was charged with methylmagnesium chloride (134 g, 1.79 mol, 3M solution in THF) dropwise at −5~−10° C. in 1 hour, the white solid dissolved slowly. The mixture was stirred at −5~−10° C. for another 1 hour. Then to the mixture was charged with 4N aqueous HCl (680 mL) and the mixture was stirred at room temperature for 10 minutes. To the mixture was charged with MTBE (1.02 L) and the mixture was stirred at room temperature for another 10 minutes. Two layers separated, the organic layer was washed with water (1 L) and sat. NaCl (1 L) sequentially. The organic layer was filtered through a $Na_2SO_4$ pad, and concentrated under reduced pressure to give Example 1 (345 g, purity: 94.98%, yield: 90%) as a colorless oil, which was directly used for the preparation of Example 2. MS m/e=246.3 [M+H]+. $^1$H NMR (400 MHz,) δ=7.67 (d, J=7.9 Hz, 1H), 7.34 (d, J=7.4 Hz, 1H), 7.34 (d, J=7.4 Hz, 1H), 7.33 (t, J=7.4 Hz, 1H), 7.33 (t, J=7.4 Hz, 1H), 7.29 (t, J=7.4 Hz, 1H), 5.29 (d, J=7.9 Hz, 1H), 5.21 (s, 2H), 4.70 (qt, J=6.2, 6.8 Hz, 1H), 2.71 (dd, J=6.8, 16.6 Hz, 1H), 2.36 (dd, J=6.8, 16.6 Hz, 1H), 1.19 (d, J=6.2 Hz, 3H).

Example 2

O1-benzyl O3-ethyl 2-methyl-4-oxo-2,3-dihydropyridine-1,3-dicarboxylate

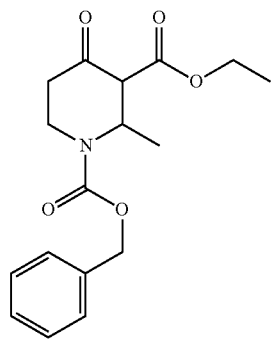 [SMILES: CCOC(=O)C1C(=O)CCN(C(=O)OCc2ccccc2)C1C]

Preparation of O1-benzyl O3-ethyl 2-methyl-4-oxo-2,3-dihydropyridine-1,3-dicarboxylate Method A)

To a 5 L jacket reactor was charged with benzyl 2-methyl-4-oxo-2,3-dihydropyridine-1-carboxylate (350 g, 1.43 mol, Example 1) and THF (1.05 L, super dry, stabilized with BHT) at room temperature. The mixture was cooled to 0~5° C. using Huber Chiller. To the mixture was charged with LiHMDS (478 g, 2.85 mol, 1M in THF) at 0~5° C. The addition was maintained for 15 minutes, and the reaction temperature was changed from 3° C. to 9° C. The mixture was agitated using a magnetic stirrer at 0~5° C. for 60 minutes. Then to the mixture was charged with ethyl (diethoxyphosphoryl)formate (318 g, 1.51 mol) at 0~5° C. The addition was maintained for 5 minutes, and the reaction temperature was then changed from 3° C. to 12° C. The mixture was stirred at 0~5° C. for another 1 hour. Then to the mixture was charged with sat. $NH_4Cl$ (50 mL) at 0~5° C. After stirring at room temperature for 10 minutes, the mixture was extracted with IPAc (160 mL). The organic layer was washed with water (150 mL) and sat. NaCl (1.5 L). The organic layer was filtered through a $Na_2SO_4$ pad, and concentrated under reduced pressure to give Example 2 (410 g, purity: 90%, yield: 87%) as a light yellow oil, which was directly used for the preparation of Example 3. MS m/e=318.3 [M+H]+. $^1$H NMR (400 MHz,) δ=7.77 (d, J=8.4 Hz, 1H), 7.34 (d, J=7.4 Hz, 1H), 7.34 (d, J=7.4 Hz, 1H), 7.33 (t, J=7.4 Hz, 1H), 7.33 (t, J=7.4 Hz, 1H), 7.29 (t, J=7.4 Hz, 1H), 5.59 (d, J=8.4 Hz, 1H), 5.23 (s, 2H), 4.85 (qd, J=6.2, 8.1 Hz, 1H), 4.13 (dq, J=−11.4, 7.1 Hz, 1H), 4.13 (dq, J=−11.4, 7.1 Hz, 1H), 3.58 (d, J=8.1 Hz, 1H), 1.42 (d, J=6.2 Hz, 3H), 1.20 (t, J=7.1 Hz, 3H)

Method B)

The title compound was prepared in analogy to Method A) of Example 2, replacing ethyl (diethoxyphosphoryl)formate with ethyl chlorocarbonate (yield 31%, purity 56%). MS m/e=318.3 [M+H]$^+$.

Example 3

O1-benzyl O3-ethyl 2-methyl-4-oxo-piperidine-1,3-dicarboxylate

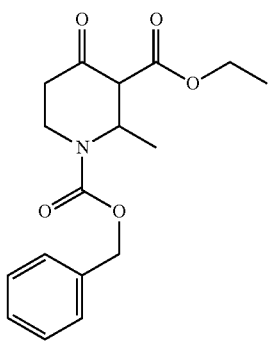 [SMILES: CCOC(=O)C1C(=O)CCN(C(=O)OCc2ccccc2)C1C]

Preparation of O1-benzyl O3-ethyl 2-methyl-4-oxo-piperidine-1,3-dicarboxylate To a 5 L jacket reactor was charged with O1-benzyl O3-ethyl 2-methyl-4-oxo-2,3-dihydropyridine-1,3-dicarboxylate (260 g, 819 mmol, Example 2), Acetic acid (2.08 L) and Zinc powder (161 g, 2.46 mol) at room temperature. The mixture was agitated using a magnetic stirrer at 65~70° C. for 3 hours. The mixture was cooled to room temperature and filtered through a pad of celite to remove Zn. The mixture was concentrated under reduced pressure to remove acetic acid. To the mixture was charged with IPAc (150 mL) and sat. Na$_2$CO$_3$ (100 mL). The organic layer was washed with sat. Na$_2$CO$_3$ (80 mL*2), then sat. NaCl (100 mL*2), dried over Na$_2$SO$_4$, concentrated under reduced pressure to give the desired product as a brown oil. The organic layer was filtered through a Na$_2$SO$_4$ pad, and concentrated under reduced pressure to give Example 3 (229 g, purity: 86.3%, yield: 88%) as a light brown oil, which was directly used for the preparation of Example 4. MS m/e=320.4 [M+H]+·−$^1$H NMR (400 MHz,) δ=7.32 (d, J=7.4 Hz, 1H), 7.32 (d, J=7.4 Hz, 1H), 7.31 (t, J=7.4 Hz, 1H), 7.31 (t, J=7.4 Hz, 1H), 7.31 (t, J=7.4 Hz, 1H), 5.11 (s, 2H), 4.77 (qd, J=6.2, 8.1 Hz, 1H), 4.14 (dq, J=−11.4, 7.1 Hz, 1H), 4.14 (dq, J=−11.4, 7.1 Hz, 1H), 3.57 (ddd, J=4.5, 7.5, 13.5 Hz, 1H), 3.53 (ddd, J=3.5, 4.5, 13.5 Hz, 1H), 3.48 (d, J=8.1 Hz, 1H), 2.58 (ddd, J=3.5, 4.5, 16.0 Hz, 1H), 2.58 (ddd, J=4.5, 7.5, 16.0 Hz, 1H), 1.31 (d, J=6.2 Hz, 3H), 1.21 (t, J=7.1 Hz, 3H).

Example 4

Benzyl 4-hydroxy-5-methyl-2-pyrimidin-2-yl-7,8-dihydro-5H-pyrido[4,3-d]pyrimidine-6-carboxylate

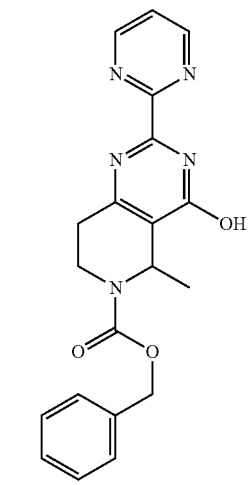 [SMILES: CC1c2c(O)nc(-c3ncccn3)nc2CCN1C(=O)OCc1ccccc1]

Preparation of benzyl 4-hydroxy-5-methyl-2-pyrimidin-2-yl-7,8-dihydro-5H-pyrido[4,3-d]pyrimidine-6-carboxylate Method A)

To a 5 L jacket reactor was charged with 1-benzyl 3-ethyl 2-methyl-4-oxopiperidine-1,3-dicarboxylate (340 g, 1.06 mol, Example 3), pyrimidine-2-carboximidamide hydrochloride (169 g, 1.06 mol), Trifluoroethanol (3.4 L) and K$_2$CO$_3$ anhydrous (367 g, 2.66 mol) at room temperature. The mixture was agitated using a magnetic stirrer at 65~70° C. for 17 hours. To the mixture was charged with water (20 mL) and IPAc (30 mL) at room temperature. The aqueous layer was re-extracted with EA (30 mL). Then the organic layer was washed with sat. NaCl (50 mL). The organic layer was filtered through a Na$_2$SO$_4$ pad, and concentrated under reduced pressure to give Example 4 (341 g, purity: 95%, yield: 85%) as a light yellow solid, which was directly used for the preparation of Example 5. MS m/e=378.4 [M+H]+. $^1$H NMR (400 MHz,) δ=8.95 (d, J=4.9 Hz, 2H), 7.41 (t, J=4.9 Hz, 1H), 7.31 (t, J=7.4 Hz, 1H), 7.31 (t, J=7.4 Hz, 1H), 7.31 (t, J=7.4 Hz, 1H), 7.30 (d, J=7.4 Hz, 1H), 7.30 (d, J=7.4 Hz, 1H), 5.85 (q, J=6.8 Hz, 1H), 5.13 (d, J=12.9 Hz, 1H), 5.13 (d, J=12.9 Hz, 1H), 4.11 (td, J=6.1, 13.3 Hz, 1H), 4.04 (td, J=6.1, 13.3 Hz, 1H), 3.19 (td, J=6.1, 15.0 Hz, 1H), 3.12 (td, J=6.1, 15.0 Hz, 1H), 1.68 (d, J=6.8 Hz, 3H).

Method B)

The title compound was prepared in analogy to Method A) of Example 4, replacing trifluoroethanol with Ethanol (yield: 38%, purity: 72%). MS m/e=378.4 [M+H]$^+$.

Example 5

Benzyl 4-chloro-5-methyl-2-pyrimidin-2-yl-7,8-dihydro-5H-pyrido[4,3-d]pyrimidine-6-carboxylate

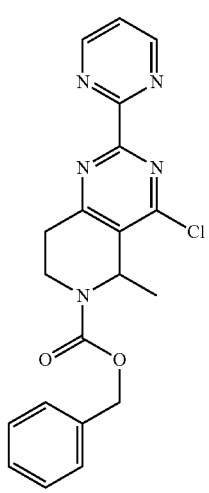 [SMILES: CC1c2c(Cl)nc(-c3ncccn3)nc2CCN1C(=O)OCc1ccccc1]

Preparation of benzyl 4-chloro-5-methyl-2-pyrimidin-2-yl-7,8-dihydro-5H-pyrido[4,3-d]pyrimidine-6-carboxylate To a 100 mL flask was charged with benzyl 4-hydroxy-5-methyl-2-pyrimidin-2-yl-7,8-dihydro-5H-pyrido[4,3-d]pyrimidine-6-carboxylate (10.5 g, 27.8 mmol, Example 4), Toluene (105 mL), tripropylamine (9.97 g, 69.6 mmol), NH$_4$Cl (1.49 g, 27.8 mmol) and POCl$_3$ (10.7 g, 69.6 mmol) at room temperature. The mixture was stirred at 55~60° C. for 3 hours. The mixture was cooled to room temperature. To the mixture was charged with water (30 mL) to quench the reaction. EA (80 mL) was also added to the reaction mixture. After stirring at room temperature for 5 minutes, two layers separated. The aqueous layer was adjusted to pH 7~8 by adding 2N NaOH (15 mL), then extracted with EA (50 mL). The organic layer was combined, and washed with 10% NaCl (50 mL) and sat. NaCl (80 mL). The organic layer was filtered through a Na$_2$SO$_4$ pad, and concentrated under reduced pressure to give Example 5 (9.3 g, purity: 90%, yield: 83%) as a light brown solid, which was directly used for the preparation of Example 6. MS m/e=396.8 [M+H]+·− −$^1$H NMR (400 MHz,) δ=9.00 (d, J=4.9 Hz, 2H), 7.41 (t, J=4.9 Hz, 1H), 7.31 (t, J=7.4 Hz, 1H), 7.31 (t, J=7.4 Hz, 1H), 7.31 (t, J=7.4 Hz, 1H), 7.30 (d, J=7.4 Hz, 1H), 7.30 (d, J=7.4 Hz, 1H), 5.87 (q, J=6.8 Hz, 1H), 5.13 (d, J=12.9 Hz, 1H), 5.13 (d, J=12.9 Hz, 1H), 4.17 (td, J=6.1, 13.3 Hz, 1H), 4.10 (td, J=6.1, 13.3 Hz, 1H), 3.28 (td, J=6.1, 15.0 Hz, 1H), 3.21 (td, J=6.1, 15.0 Hz, 1H), 1.72 (d, J=6.8 Hz, 3H).

Example 6

5-methyl-2-pyrimidin-2-yl-5,6,7,8-tetrahydropyrido[4,3-d]pyrimidine

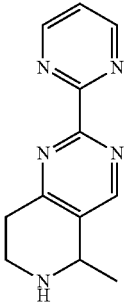

Preparation of 5-methyl-2-pyrimidin-2-yl-5,6,7,8-tetrahydropyrido[4,3-d]pyrimidine To a 25 mL flask was charged with benzyl 4-chloro-5-methyl-2-pyrimidin-2-yl-7,8-dihydro-5H-pyrido[4,3-d]pyrimidine-6-carboxylate (3.2 g, 8.08 mmol, Example 5), EtOH (32 mL), water (8 mL), NH$_3$·H$_2$O (8 mL) and Palladium 10% on carbon (wetted with ca. 55% water) (300 mg, 2.82 mmol) at room temperature. The mixture was stirred at room temperature under H$_2$ for 20 hours. The mixture was filtered through celite, washed with EtOH (20 mL*2). The filtration was concentrated under reduced pressure to give the desired product, and the solid was then re-slurried in IPAc (25 mL) to give Example 6 (1.8 g, purity: 95%, yield: 95%) as a yellow solid, which was directly used for the preparation of Example 7. MS m/e=228.3 [M+H]+. $^1$H NMR (400 MHz,) δ=9.00 (d, J=4.9 Hz, 2H), 8.86 (s, 1H), 7.41 (t, J=4.9 Hz, 1H), 4.41 (dq, J=2.6, 6.7 Hz, 1H), 3.61 (dtd, J=2.8, 6.2, 12.5 Hz, 1H), 3.33 (dtd, J=3.7, 6.2, 12.5 Hz, 1H), 3.24 (dt, J=−15.3, 6.2 Hz, 1H), 3.17 (dt, J=−15.3, 6.2 Hz, 1H), 1.40 (d, J=6.7 Hz, 3H).

Example 7

6-(6-fluoro-4-methoxy-2-pyridyl)-5-methyl-2-pyrimidin-2-yl-7,8-dihydro-5H-pyrido[4,3-d]pyrimidine

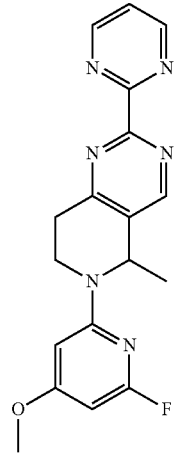 [SMILES: COc1cc(F)nc(N2CCc3nc(-c4ncccn4)ncc3C2C)c1]

Preparation of 6-(6-fluoro-4-methoxy-2-pyridyl)-5-methyl-2-pyrimidin-2-yl-7,8-dihydro-5H-pyrido[4,3-d]pyrimidine To A 5 L reactor was charged with 5-methyl-2-pyrimidin-2-yl-5,6,7,8-tetrahydropyrido[4,3-d]pyrimidine (500 g, 1.30 mol, Example 6), CsF (1.36 kg, 8.95 mol) and 1-butyl-3-methylimidazolium tetrafluoroborate (1.68 L, 3.3V) under $N_2$. To the mixture, 2,6-difluoro-4-methoxy-pyridine (486 g, 3.35 mol) was added. The reaction mixture was stirred at 90° C. for 48 hours. Then the mixture was cooled in an ice/water bath, and to the mixture was charged with water (18 L). The mixture was extracted with EtOAc (18 L) for twice. The combined organic layer was washed with brine (30 L) and concentrated under reduced pressure to give the crude product. The crude product was purified through silical gel column to give Example 7 (345 g, purity: 94.98%, yield: 70%) as a colorless oil, which was directly used for the preparation of Example 8. MS m/e=353.1 [M+H]+. $^1$H NMR (400 MHz,) δ=9.00 (d, J=4.9 Hz, 2H), 8.81 (s, 1H), 7.41 (t, J=4.9 Hz, 1H), 6.09 (s, 1H), 5.83 (d, J=10.8 Hz, 1H), 4.83 (q, J=6.6 Hz, 1H), 4.16 (td, J=6.2, 13.1 Hz, 1H), 4.09 (td, J=6.2, 13.1 Hz, 1H), 3.90 (s, 3H), 3.19 (dt, J=−15.3, 6.2 Hz, 1H), 3.19 (dt, J=−15.3, 6.2 Hz, 1H), 1.64 (d, J=6.6 Hz, 3H).

Example 8

(5R)-6-(6-fluoro-4-methoxy-2-pyridyl)-5-methyl-2-pyrimidin-2-yl-7,8-dihydro-5H-pyrido[4,3-d]pyrimidine

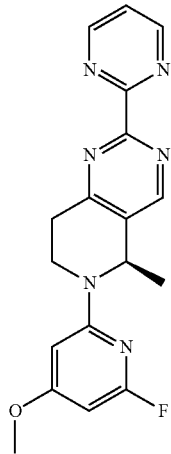 [SMILES: COc1cc(F)nc(N2CCc3nc(-c4ncccn4)ncc3[C@H]2C)c1]

Preparation of (5R)-6-(6-fluoro-4-methoxy-2-pyridyl)-5-methyl-2-pyrimidin-2-yl-7,8-dihydro-5H-pyrido[4,3-d]pyrimidine The 6-(6-fluoro-4-methoxy-2-pyridyl)-5-methyl-2-pyrimidin-2-yl-7,8-dihydro-5H-pyrido[4,3-d]pyrimidine (450 g, 0.85 mol, Example 7, light yellow solid) was diluted to a solution in methanol (2.09 Kg, 25 wt %). This solution was separated by chiral SFC, and the condition was as following, Column: Chiralcel OD, 300×50 mm I.D., 10 um; Mobile phase: A for $CO_2$ and B for methanol; Gradient: B 40%; Flow rate: 200 mL/min; Back pressure: 100 bar; Column temperature: 38° C.; Wavelength: 220 nm; Cycle time: ~10 min. The crude product (205 g) was dissolved in methanol (610 mL) again. To the solution was charged with activated charcoal (Darco @60, 25 g) and the mixture was stirred at 50° C. for 1 hour, then filtrated through diatomite Pad. Methanol was removed under reduced pressure and further removed by azeotroping with IPAc. The solid was collected by filtration and the cake was washed with IPAc. The wet cake was dried at 40° C. in vacuum with nitrogen fleet for 20 hours to give the desired product. The white solid was used directly, giving 184.8 g of (5R)-6-(6-fluoro-4-methoxy-2-pyridyl)-5-methyl-2-pyrimidin-2-yl-7,8-dihydro-5H-pyrido[4,3-d]pyrimidine. The purity was 98.8%, the yield was 40.7%. MS m/e=353.1 [M+H]+. $^1$H NMR (400 MHz,) δ=9.00 (d, J=4.9 Hz, 2H), 8.81 (s, 1H), 7.41 (t, J=4.9 Hz, 1H), 6.09 (s, 1H), 5.83 (d, J=10.8 Hz, 1H), 4.83 (q, J=6.8 Hz, 1H), 4.21 (dt, J=−12.5, 5.7 Hz, 1H), 4.05 (dt, J=−12.5, 5.7 Hz, 1H), 3.90 (s, 3H), 3.23 (dt, J=−15.3, 5.7 Hz, 1H), 3.17 (dt, J=−15.3, 5.7 Hz, 1H), 1.64 (d, J=6.8 Hz, 3H).

Example 9 Comparative Study

The advantages from this process in this invention, compared to the one disclosed in WO2016/177655, are showed in the following aspects:

(a) The overall production yield of (5R)-6-(6-fluoro-4-methoxy-2-pyridyl)-5-methyl-2-pyrimidin-2-yl-7,8-dihydro-5H-pyrido[4,3-d]pyrimidine was increased from 1.5% to 13% with total 8 steps synthesis.

The individual step yields of Example 1 to Example 8 were shown in Table 1. The overall yield in the longest linear sequence was 13.1%.

TABLE 1

| Yield of Each Step from Example 1 to Example 8 ||
| --- | --- |
| The overall yield for the new process is calculated as follows: | Yield achieved |
| Example 1 | 90% |
| Example 2 | 87% |
| Example 3 | 88% |
| Example 4 | 85% |
| Example 5 | 83% |
| Example 6 | 95% |
| Example 7 | 70% |
| Example 8 | 41% |

According to the synthetic procedure disclosed in WO2016/177655, the overall yield was 1.5% with the details below:

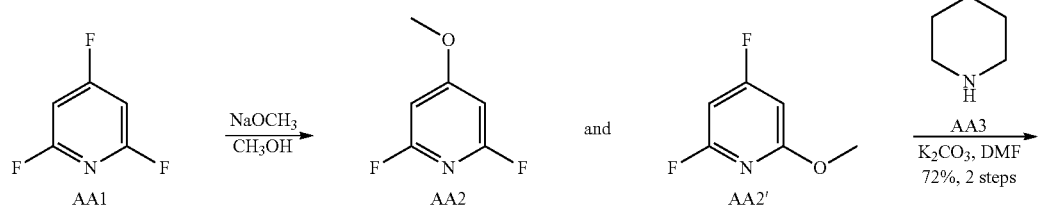

-continued
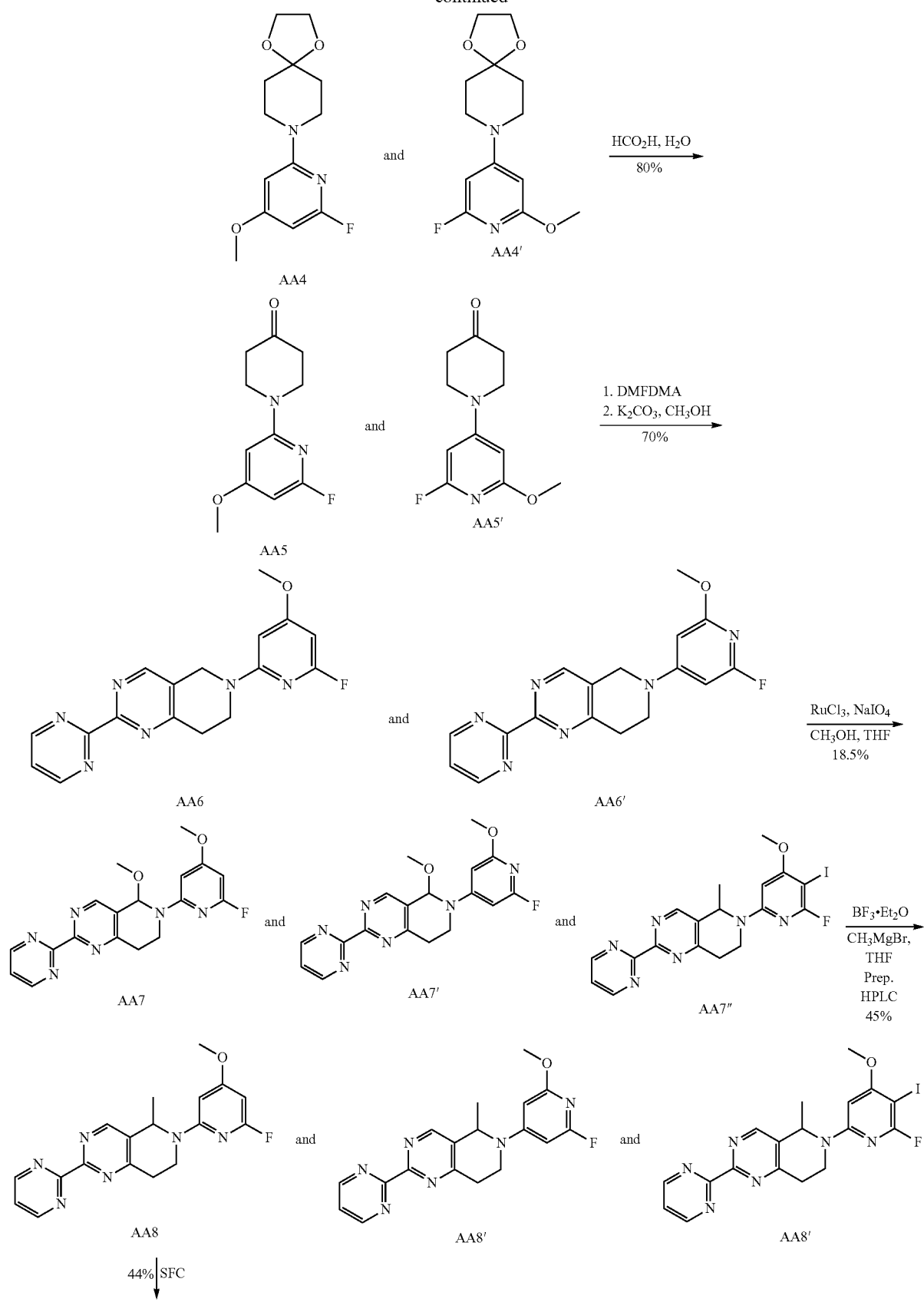

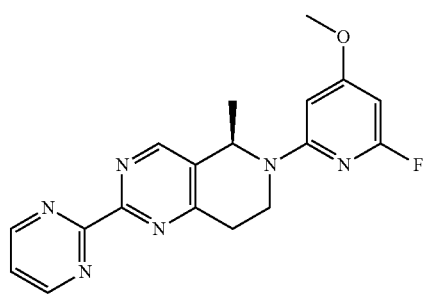

and

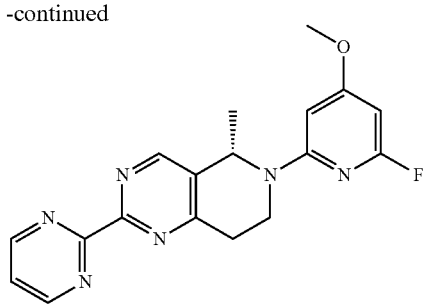

(b) The regioselectivity issue was solved through the sequence of double bond's occupation, thus the overall synthesis efficiency and yield were significantly improved.

(c) The number of column purification was reduced from 3 to 1.

(d) The synthesis of Example 6 is achieved through selective hydrogenation, and the production yield is increased to 95%.

(e) A greener and more efficient synthesis procedure was innovatively developed with Ionic Liquids and CsF condition for step g in this invention. The ionic liquid, 1-butyl-3-methylimidazolium tetrafluoroborate ([BMIM][BF$_4$]), is an excellent media as a green solvent for the N-Arylation reaction and CsF was identified as an only effective base for this high yield reaction after extensive base screening. The advantages for this developed new reaction condition include removed non-green organic solvent, DMSO or DMF, with much higher yield, lower reaction temperature, less byproducts and easier work-up of purification so to significantly improve reaction scalability for the manufacture process of the API supply.

The invention claimed is:

1. A process for preparing a compound of formula (I),

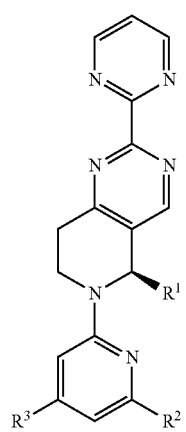

(I)

wherein:
R$^1$ is C$_{1-6}$alkyl;
R$^2$ is C$_{1-6}$alkyl or halogen; and
R$^3$ is C$_{1-6}$alkyl or C$_{1-6}$alkoxy;
or a pharmaceutically acceptable salt thereof;

the process comprising one or more of the following steps:

a) formation of dihydropyridine (III);

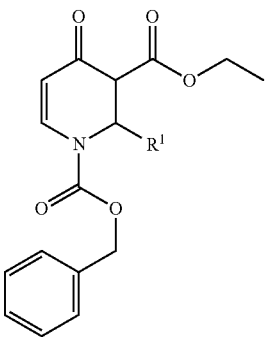

(III)

b) formation of dihydropyridine (IV) via the alkylation reaction of the dihydropyridine (III) and ethyl diethoxyphosphorylformate;

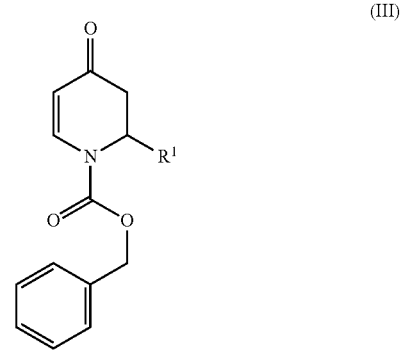

(IV)

c) formation of piperidine (V) via the reduction reaction of the compound of formula (IV);

(V)

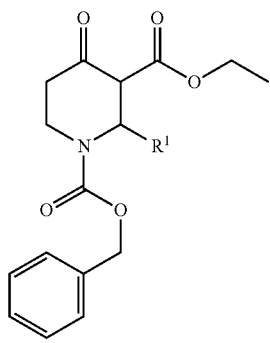

d) formation of the compound of formula (VI) via the cyclization reaction of piperidine (V) and pyrimidine-2-carboxamidine;

(VI)

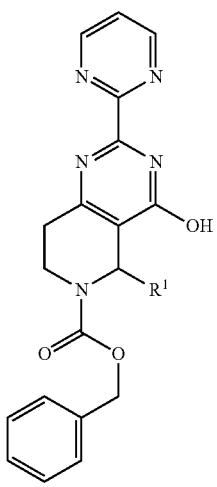

e) formation of the compound of formula (VII) via chlorination of the compound of formula (VI);

(VII)

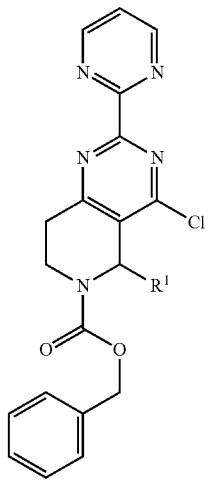

f) formation of the compound of formula (VIII) via selective hydrogenation of the compound of formula (VII);

(VIII)

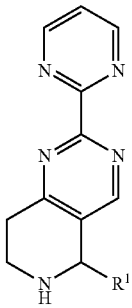

g) formation of the compound of formula (X) by N-alkylation of the compound of formula (VIII) with the compound of formula (IX);

(IX)

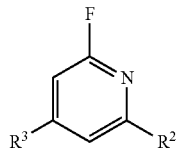

(X)

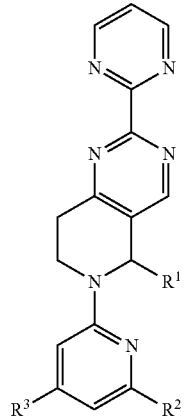

h) SFC separation of the compound of formula (X) to afford the compound of formula (I).

2. The process according to claim 1, wherein $R^1$ is $C_{1-6}$ alkyl, $R^2$ is halogen, and $R^3$ is $C_{1-6}$alkoxy.

3. The process according to claim 2, wherein $R^1$ is methyl; $R^2$ is F; and $R^3$ is methoxy.

4. The process according to claim 1, wherein:
the formation of the dihydropyridine (III) in a) is performed in the presence of a metal reagent in an organic solvent,
wherein: the metal reagent is selected from methyl, ethyl and isopropyl Grignard reagent; and
the organic solvent is selected from MTBE, THF, $Et_2O$ and Me-THF.

5. The process according to claim 1, wherein:
the formation of the compound of formula (IV) in b) is performed in the presence of a base in an organic solvent, wherein;

the base is selected from selected from t-BuONa, LDA, LiHMDS and NaHMDS; and the organic solvent is selected from MTBE, THF, Et$_2$O and MeTHF.

6. The process according to claim 1, wherein:

the formation of the piperidine (V) in c) is performed in the presence of a reductive reagent in an organic solvent, wherein:

the reductive reagent is selected from Fe powder, Zn powder and NaBH$_4$; and the organic solvent is selected from MeOH, EtOH, AcOH and formic acid.

7. The process according to claim 1, wherein:

the formation of the compound of formula (VI) in d) is performed in the presence of a base in an organic solvent, wherein:

the base is selected from DIPEA, Cs$_2$CO$_3$, K$_2$CO$_3$ and K$_3$PO$_4$; and the organic solvent is selected from isopropyl alcohol, methanol, trifluoroethanol and ethanol.

8. The process according to claim 1 wherein:

the formation of the compound of formula (VII) in e) is performed in the presence of a base in an organic solvent, wherein:

the base is selected from TEA, DIPEA and tripropylamine; and the organic solvent is selected from DCM, MTBE, toluene and 1,2-dimethoxyethane.

9. The process according to claim 1, wherein:

the formation of the compound of formula (VIII) in f) is performed in the presence of a base in an organic solvent, wherein:

the base is selected from DIPEA, tripropylamine, NH$_3$·H$_2$O and TEA; and the organic solvent is selected from IPAc, isopropyl alcohol, ethanol and methanol.

10. The process according to claim 1, wherein:

the formation of the compound of formula (X) in g) is performed in the presence of a base in an organic solvent, wherein:

the base is selected from DIPEA, TEA, tripropylamine, 2,2,6,6-Tetramethylpiperidine, N,N-dicyclohexylmethylamine, DBU, NMM, triethanolamine, pyridine, potassium tert-butylate, magnesium tert-butylate, K$_3$PO$_4$, K$_2$CO$_3$, Cs$_2$CO$_3$, CsF, and CaO; and the organic solvent is selected from IPA, trifluoroethanol, 4-Methyl-2-pentanol, 1,2-propandiol, ACN, DMF, DMAc, DMSO, sulfolane, NMP, pyridine, and 1-butyl-3-methylimidazolium tetrafluoroborate.

11. The process according to claim 10, wherein the base in g) is CsF.

12. The process according to claim 10, wherein the organic solvent in g) is 1-butyl-3-methylimidazolium tetrafluoroborate.

13. The process according to claim 1, wherein: the compound of formula (I) in h) is separated out by a chiral column, wherein the chiral column is selected from Chiralcel OD and CHIRALPAK AD-3.

14. The process according to claim 4, wherein the metal reagent in a) is methyl Grignard reagent.

15. The process according to claim 4, wherein the organic solvent in a) is THF.

16. The process according to claim 5, wherein the base in b) is LiHMDS.

17. The process according to claim 5, wherein the organic solvent in b) is THF.

18. The process according to claim 6, wherein the reductive agent in c) is Zn powder.

19. The process according to claim 6, wherein the organic solvent in c) is AcOH.

20. The process according to claim 7, wherein the base in d) is K$_2$CO$_3$.

21. The process according to claim 7, wherein the organic solvent in d) is trifluoroethanol.

22. The process according to claim 8, wherein the base in e) is tripropylamine.

23. The process according to claim 8, wherein the organic solvent in e) is toluene.

24. The process according to claim 9, wherein the base in f) is NH$_3$·H$_2$O.

25. The process according to claim 9, wherein the organic solvent in f) is ethanol.

26. The process according to claim 10, wherein the base in g) is K$_3$PO$_4$.

27. The process according to claim 10, wherein the organic solvent in g) is NMP.

28. The process according to claim 13, wherein the chiral column is Chiralcel OD.

\* \* \* \* \*